(12) United States Patent
Wan et al.

(10) Patent No.: US 9,968,616 B2
(45) Date of Patent: May 15, 2018

(54) DISCOVERY OF FDA-APPROVED DRUGS AS INHIBITORS OF FATTY ACID BINDING PROTEIN 4 USING MOLECULAR DOCKING SCREENING

(71) Applicant: The Chinese University of Hong Kong, Hong Kong (CN)

(72) Inventors: David Chi Cheong Wan, Hong Kong (CN); Yan Wang, Hong Kong (CN); Wai Kit Law, Hong Kong (CN); Jian Shu Hu, Liou Ning (CN); Tsz Ming Ip, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 0 days. days.

(21) Appl. No.: 14/920,892

(22) Filed: Oct. 23, 2015

(65) Prior Publication Data
US 2016/0113937 A1    Apr. 28, 2016

Related U.S. Application Data

(60) Provisional application No. 62/068,625, filed on Oct. 25, 2014.

(51) Int. Cl.
*A61K 31/5383* (2006.01)
*A61K 31/00* (2006.01)

(52) U.S. Cl.
CPC .......... *A61K 31/5383* (2013.01); *A61K 31/00* (2013.01)

(58) Field of Classification Search
CPC .................................................. A61K 31/536
USPC ...................................................... 514/230.2
See application file for complete search history.

(56) References Cited

U.S. PATENT DOCUMENTS

| 9,682,093 B2 * | 6/2017 | Singh ................. A61K 31/7034 |
| 2010/0087386 A1 | 4/2010 | Dudley et al. |
| 2014/0038886 A1 | 2/2014 | Mier et al. |

FOREIGN PATENT DOCUMENTS

| WO | 2013036290 | 3/2013 |
| WO | WO-2014159510 | * 10/2014 |

OTHER PUBLICATIONS

Adida, A.; Spener, F., Adipocyte-Type Fatty Acid-Binding Protein as Inter-Compartmental Shuttle for Peroxisome Proliferator Activated Receptor Gamma Agonists in Cultured Cell. Biochim Biophys Acta 2006, 1761, 172-181.
Ahmadian, M.; Suh, J. M.; Hah, N.; Liddle, C.; Atkins, A. R.; Downes, M.; Evans, R. M., Ppargamma Signaling and Metabolism: The Good, the Bad and the Future. Nat Med 2013, 19, 557-566.
Bak, M.; Fransen, A.; Janssen, J.; van Os, J.; Drukker, M., Almost All Antipsychotics Result in Weight Gain: A Meta-Analysis. PLoS One 2014, 9, e94112.
Barf, T.; Lehmann, F.; Hammer, K.; Haile, S.; Axen, E.; Medina, C.; Uppenberg, J.; Svensson, S.; Rondahl, L.; Lundback, T., N-Benzyl-Indolo Carboxylic Acids: Design and Synthesis of Potent and Selective Adipocyte Fatty-Acid Binding Protein (a-Fabp) Inhibitors. Bioorg Med Chem Lett 2009, 19, 1745-1748.
Boden, G., Obesity, Insulin Resistance and Free Fatty Acids. Curr Opin Endocrinol Diabetes Obes 2011, 18, 139-143.
Boord, J. B.; Fazio, S.; Linton, M. F., Cytoplasmic Fatty Acid-Binding Proteins: Emerging Roles in Metabolism and Atherosclerosis. Curr Opin Lipidol 2002, 13, 141-147.
Cai, H. Y.; Wang, T.; Zhao, J. C.; Sun, P.; Yard, G. R.; Ding, H. P.; Li, Y. X.; Wang, H. Y.; Zhu, W. L.; Chen, K. X., Benzbromarone, an Old Uricosuric Drug, Inhibits Human Fatty Acid Binding Protein 4 in Vitro and Lowers the Blood Glucose Level in Db/Db Mice. Acta Pharmacol Sin 2013, 34, 1397-1402.
Charleston, L. t., Burning Mouth Syndrome: A Review of Recent Literature. Curr Pain Headache Rep 2013, 17, 336.
Friedrich, L. V.; Dougherty, R., Fatal Hypoglycemia Associated with Levofloxacin. Pharmacotherapy 2004, 24, 1807-1812.
Furuhashi, M.; Hotamisligil, G. S., Fatty Acid-Binding Proteins: Role in Metabolic Diseases and Potential as Drug Targets. Nat Rev Drug Discov 2008, 7, 489-503.
Furuhashi, M.; Tuncman, G.; Gorgun, C. Z.; Makowski, L.; Atsurni, G.; Vaillancourt, E.; Kono, K.; Babaev, V. R.; Fazio, S.; Linton, M. F.; Sulsky, R.; Robl, J. A.; Parker, R. A.; Hotamisligil, G. S., Treatment of Diabetes and Atherosclerosis by Inhibiting Fatty-Acid-Binding Protein Ap2. Nature 2007, 447, 959-965.
Garin-Shkolnik, T.; Rudich, A.; Hotamisligil, G. S.; Rubinstein, M., Fabp4 Attenuates Ppargamma and Adipogenesis and is Inversely Correlated with Ppargamma in Adipose Tissues. Diabetes 2014, 63, 900-911.
Gillilan, R. E.; Ayers, S. D.; Noy, N., Structural Basis for Activation of Fatty Acid-Binding Protein 4. J Mol Biol 2007, 372, 1246-1260.
Goldstein, E. J., Possible Role for the New Fluoroquinolones (Levofloxacin, Grepafloxacin, Trovafloxacin, Clinafloxacin, Sparfloxacin, and Du-6859a) in the Treatment of Anaerobic Infections: Review of Current Information on Efficacy and Safety. Clin Infect Dis 1996, 23 Suppl 1, S25-30.
Kanbay, M.; Aydogan, T.; Bozalan, R.; Isik, A.; Uz, B.; Kaya, A.; Akcay, A., A Rare but Serious Side Effect of Levofloxacin: Hypoglycemia in a Geriatric Patient. Diabetes Care 2006, 29, 1716-1717.
Karpe, F.; Dickmann, J. R.; Frayn, K. N., Fatty Acids, Obesity, and Insulin Resistance: Time for a Reevaluation. Diabetes 2011, 60, 2441-2449.
Lehmann, F.; Haile, S.; Axen, E.; Medina, C.; Uppenberg, J.; Svensson, S.; Lundback, T.; Rondahl, L.; Barf, T., Discovery of Inhibitors of Human Adipocyte Fatty Acid-Binding Protein, a Potential Type 2 Diabetes Target. Bioorg Med Chem Lett 2004, 14, 4445-4448.

(Continued)

*Primary Examiner* — Jeffrey S Lundgren
*Assistant Examiner* — Michael J Schmitt
(74) *Attorney, Agent, or Firm* — Law Offices of Albert Wai-Kit Chan, PLLC

(57) ABSTRACT

Using molecular docking screening, a few therapeutical compounds including trovafloxacin and levofloxacin have been first identified as potential inhibitors of fatty acid binding protein 4 (FABP4). The present invention provides a novel use of levofloxacin as an inhibitor of FABP4 and a drug for the treatment of metabolic diseases or a cardiovascular diseases. The present invention further provides a method of using levofloxacin to inhibit FABP4, or to inhibit adipolysis in adipocytes.

14 Claims, 5 Drawing Sheets

(56) References Cited

OTHER PUBLICATIONS

Leung, C. H.; Chan, D. S.; Kwan, M. H.; Cheng, Z.; Wong, C. Y.; Zhu, G. Y.; Fong, W. F.; Ma, D. L., Structure-Based Repurposing of FDA-Approved Drugs as Tnf-Alpha Inhibitors. ChemMedChem 2011, 6, 765-768.

Ma, D. L.; Chan, D. S.; Leung, C.H., Drug Repositioning by Structure-Based Virtual Screening. Chem Soc Rev 2013, 42, 2130-2141.

Maeda, K.; Cao, H.; Kono, K.; Gorgun, C. Z.; Furuhashi, M.; Uysal, K. T.; Cao, Q.; Atsumi, G.; Malone, H.; Krishnan, B.; Minokoshi, Y.; Kahn, B. B.; Parker, R. A.; Hotamisligil, G. S., Adipocyte/Macrophage Fatty Acid Binding Proteins Control Integrated Metabolic Responses in Obesity and Diabetes. Cell Metab 2005, 1, 107-119.

Ng, C.; Hauptman, R.; Zhang, Y.; Bourne, P. E.; Xie, L., Anti-Infectious Drug Repurposing Using an Integrated Chemical Genomics and Structural Systems Biology Approach. Pac Symp Biocomput 2014, 136-147.

Oprea, T. I.; Mestres, J., Drug Repurposing: Far Beyond New Targets for Old Drugs. AAPS J 2012, 14, 759-763.

Ringom, R.; Axen, E.; Uppenberg, J.; Lundback, T.; Rondahl, L.; Barf, T., Substituted Benzylamino-6-(Trifluoromethyl) Pyrimidin-4(1h)-Ones: A Novel Class of Selective Human a-Fabp Inhibitors. Bioorg Med Chem Lett 2004, 14, 4449-4452.

Singh, N.; Jacob, J. J., Levofloxacin and Hypoglycemia. Clin Infect Dis 2008, 46, 1127.

Sulsky, R.; Magnin, D. R.; Huang, Y.; Simpkins, L.; Taunk, P.; Patel, M.; Zhu, Y.; Stouch, T. R.; Bassolino-Klimas, D.; Parker, R.; Harrity, T.; Stoffel, R.; Taylor, D. S.; Lavoie, T. B.; Kish, K.; Jacobson, B. L.; Sheriff, S.; Adam, L. P.; Ewing, W. R.; Robl, J. A., Potent and Selective Biphenyl Azole Inhibitors of Adipocyte Fatty Acid Binding Protein (Afabp). Bioorg Med Chem Lett 2007, 17, 3511-3515.

Wang, Y.; Law, W.K.; Hu, J.S.; Lin, H.Q.; Ip, T.M.; Wan, D.C., Discovery of FDA-approved drugs as inhibitors of fatty acid binding protein 4 using molecular docking screening. J Chem Inf Model. 2014, 54:3046-50.

Wimer, S. M.; Schoonover, L.; Garrison, M. W., Levofloxacin: A Therapeutic Review. Clin Ther 1998, 20, 1049-1070.

Zhong, H. J.; Liu, L. J.; Chan, D. S.; Wang, H. M.; Chan, P. W.; Ma, D. L.; Leung, C. H., Structure-Based Repurposing of FDA-Approved Drugs as Inhibitors of Nedd8-Activating Enzyme. Biochimie 2014, 102, 211-215.

* cited by examiner

DISCOVERY OF FDA-APPROVED DRUGS AS INHIBITORS OF FATTY ACID BINDING PROTEIN 4 USING MOLECULAR DOCKING SCREENING

CROSS-REFERENCE TO RELATED APPLICATIONS

This application claims the priority of U.S. Ser. No. 62/068,625 filed Oct. 25, 2014. The entire content and disclosure of the preceding applications are incorporated by reference into this application.

Throughout this application, various references are referred to and disclosures of these publications in their entireties are hereby incorporated by reference into this application to more fully describe the state of the art to which this invention pertains.

FIELD OF THE INVENTION

This invention relates to a method for alleviating or treating metabolic diseases or cardiovascular diseases. In one embodiment, the present invention relates to a method for alleviating or treating metabolic diseases or cardiovascular diseases using compound(s) that inhibit the fatty acid binding protein 4 (FABP4).

BACKGROUND OF THE INVENTION

Fatty acids are a class of carboxylic acids with a long aliphatic tail. Many fatty acids are derived from triglycerides or phospholipids; they serve as critical sources of fuel in our body. There is accumulating evidence showing that chronically elevated plasma fatty acid leads to pathophysiological disorders. The elevated fatty acid levels in circulation are associated with the pathogenesis of diabetes, obesity and atherosclerosis (reviewed in 1-3). The intracellular trafficking of fatty acids requires a cluster of specific carrier proteins, named fatty acid-binding proteins (FABPs). Fatty acids directly bind to FABPs with high affinity, and the fatty acid-FABP complex are transported in cytoplasm for metabolic process or storage (4, 5).

The adipocyte FABP, FABP4 (aP2), is highly expressed in adipocytes. FABP4 plays an important role in various aspects of metabolic disorders, including insulin resistance, diabetes, and atherosclerosis. Insulin resistance can be observed in high-fat diet-fed mice; deficiency of FABP4 partially protects these mice against the development of insulin resistance. In addition, FABP4-deficient mice exhibits better performances in both insulin and glucose tolerance tests (6). Apart from genetic approaches, the blockade of FABP4 by small molecules could potentially mimic the phenotype of FABP4-deficient mice (6). Therefore, pharmacological agents that inhibit FABP4-mediated responses might serve as potential candidates for the treatment of insulin resistance, diabetes, and atherosclerosis (7).

FABP4 has recently been reported to interact directly with the nuclear receptor peroxisome proliferator-activated receptor γ (PPARγ), triggering the ubiquitination and the subsequent proteasomal degradation of PPARγ (8). BMS309403, the well-characterized FABP4 inhibitor, up-regulated the basal protein levels of PPARγ (9). The elevation of PPARγ induced adipogenesis in adipose tissue, which is a significant adverse effect of PPARγ activation (10). The fatty acid binding pocket of FABP4 is distinct from the interaction site of FABP4 and PPARγ (8). In this respect, BMS309403 binding to FABP4 might lead to an allosteric regulation of FABP4, and therefore resulting in the elevation of PPARγ protein expression (8).

The expenditure of research and development (R&D) increased dramatically over past two decades. The pharmaceutical industries are keen to several strategies to reduce the cost of new drug development. The strategy of U.S. Food and Drug Administration (FDA)-approved drug repurposing aims to identify new uses for existing drugs. Given that the favorable pharmacokinetic and toxicological profiles of existing drugs in human subjects have been well characterized, a collection of FDA-approved drugs can be powerful resources for new indications discovery (11-16). For example, ciclopirox olamine is a synthetic antifungal drug for topical dermatologic treatment of superficial mycoses. Recently, ciclopirox olamine has been identified as a novel intracellular iron chelator, which exhibited anticancer activity in both in vitro and in vivo studies (17). The latest clinical trials reported that ciclopirox olamine displayed biological activity, which is now in Phase I study in patients with advanced hematologic malignancies (18).

In the present invention, a ligand library containing about 1500 compounds from FDA-approved drugs was compiled to search for ligand of human FABP4 for potential drugs of metabolic disorders. The present invention hereby describes the uses of small chemical molecules as FABP4 inhibitors and drugs for the treatment of metabolic diseases or cardiovascular diseases.

BRIEF SUMMARY OF THE INVENTION

The present invention provides a novel use of compound(s) as an inhibitor of fatty acid binding protein 4 (FABP4) and a drug for the treatment of metabolic diseases or cardiovascular diseases.

In one embodiment, the present invention provides a method of using a FABP4-inhibiting compound to alleviate or treat metabolic syndromes or diseases, or cardiovascular diseases.

In another embodiment, the present invention provides a method of using a FABP4-inhibiting compound to alleviate or treat syndromes or diseases that are responsive to the FABP4 inhibition.

In one embodiment, the present invention provides a method of using levofloxacin to alleviate or treat metabolic diseases or cardiovascular diseases, or other syndromes or diseases that are responsive to the FABP4 inhibition.

BRIEF DESCRIPTION OF THE DRAWINGS

FIG. 1A shows the workflow chart of the screening and analysis. FIG. 1B depicts the chemical structure of levofloxacin. FIG. 1C lists the critical amino acid residues for the binding between ligands and FABP4 in four crystal structure models of human FABP4. Inhibitors in each of the four crystal structures were used as benchmarks. FIG. 1D illustrates the favorable binding positions of levofloxacin (stick) with lowest binding free energy in the inhibitor-binding site of human FABP4 (ribbon cartoon). Amino acid residues of FABP4 that may involve in the binding are shown as line.

FIG. 3A shows the dose-response curves of levofloxacin and arachidonic acid (AA) in a FABP4 activity inhibition assay.

FIG. 3B shows the inhibition of basal and isoproterenol-stimulated adipolysis in 3T3-L1 cells treated by levofloxacin or benzbromarone (BBR) at 10 μM. [P<0.05; compared with the control group. #, P<0.05; compared with the isoproterenol-treated group].

FIG. 3C shows the viability of 3T3-L1 cells after the levofloxacin or benzbromarone (BBR) treatment at 10 μM.

FIG. 3D shows the results of Oil Red 0 staining of 3T3-L1 cells after the treatment with levofloxacin for 6 days. FIG. 3E shows a western blot analysis detecting the PPARγ and β-actin in the cell lysate of 3T3-L1 cells after treatment with levofloxacin for 6 days.

DETAILED DESCRIPTION OF THE INVENTION

Figure 1A:
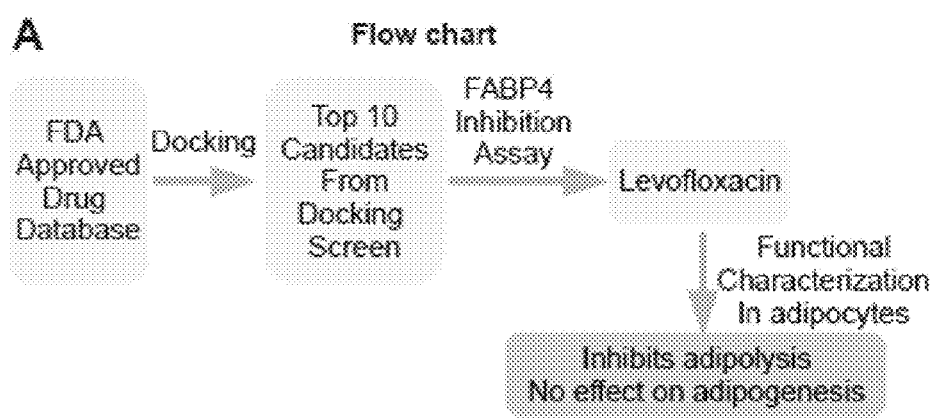
FIGS. 1A-1D show one embodiment of the molecular docking screening and analysis described in the present invention.

The present invention provides a use of compound(s) as an inhibitor of fatty acid binding protein 4 (FABP4) and a drug for the treatment of metabolic diseases, or a cardiovascular diseases.

In another embodiment, the present invention provides a method of using a FABP4-inhibiting compound to alleviate or treat syndromes or diseases that are responsive to the FABP4 inhibition.

In one embodiment, the present invention provides uses of levofloxacin or salts thereof as a FABP4-inhibiting compound for alleviating or treating metabolic or cardiovascular diseases. The IUPAC name of levofloxacin is (S)-9-fluoro-2,3-dihydro-3-methyl-10-(4-methylpiperazin-1-yl)-7-oxo-7H-pyrido[1,2,3-de]-1,4-benzoxazine-6-carboxylic acid having the structure of:

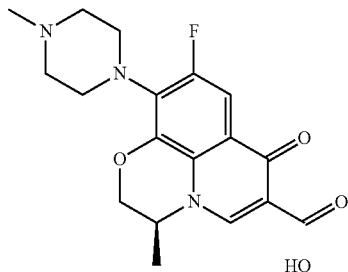

In one embodiment, the present invention provides a method of using levofloxacin or salts thereof to alleviate or treat metabolic syndromes or diseases including, but are not limited to, insulin resistance, diabetes, obesity, high blood pressure, high fasting plasma glucose, high serum triglycerides, and low high-density lipoprotein (HDL) levels.

In another embodiment, the metabolic syndrome or disease is a syndrome or disease that is related to any metabolic process mediated by the fatty acid binding protein 4 (FABP4).

In one embodiment, the present invention provides a method of using levofloxacin or salts thereof to alleviate or treat cardiovascular diseases including, but are not limited to, atherosclerosis, coronary artery diseases, angina, myocardial infarction, stroke, hypertensive heart disease, cardiomyopathy, peripheral artery disease and venous thrombosis.

In another embodiment, the cardiovascular disease is a heart or blood vessel disease that is related to any metabolic process mediated by the fatty acid binding protein 4 (FABP-4).

It will be appreciated by persons skilled in the art that the uses of levofloxacin disclosed herein may be used for the treatment of metabolic or cardiovascular diseases but its application could be extended to any disease which can be treated, alleviated or prevented by the inhibition of FABP4.

In one embodiment, the present invention provides a method of inhibiting adipolysis in a subject, the method comprises administering to a subject an effective amount of a pharmaceutical composition comprising levofloxacin. In one embodiment, the adipolysis is the degradation or hydrolysis of triglycerides in adipocytes.

In one embodiment, the present invention provides a method of reducing the accumulation of lipids in a subject, the method comprises administering to a subject an effective amount of a pharmaceutical composition comprising levofloxacin.

In one embodiment, the present invention provides a method of inhibiting adipolysis or reducing the accumulation of lipids in adipocytes without inducing an adipogenesis in adipocytes.

In another embodiment, the present invention provides a method of inhibiting adipolysis or reducing the accumulation of lipids in adipocytes without increasing the protein expression of PPARγ in adipocytes.

In one embodiment, the subject is an adult or a child of human.

In one embodiment, the concentration of levofloxacin to be used is about 100 nM to 20 μM. In one embodiment, the concentration of levofloxacin is about 1-5 μM. In another embodiment, the concentration of levofloxacin is about 7.5-15 μM. In another embodiment, the concentration of levofloxacin is about 10 μM.

In one embodiment, the "effective amount" or the "therapeutically effective amount" means the amount of the pharmaceutical composition that is necessary to achieve a desired physiological effect.

In one embodiment, the pharmaceutical compositions of the present invention can be formulated as neutral or any pharmaceutically acceptable salt forms. In one embodiment, the pharmaceutical compositions of the present invention comprise levofloxacin, salts or derivatives thereof.

One of ordinary skill in the art would readily determine the appropriate route of administration and dosage form for the pharmaceutical composition comprising levofloxacin described herein.

In one embodiment, the pharmaceutical composition comprising levofloxacin is administered in combination with other active or non-active agents or compounds.

In one embodiment, the pharmaceutical composition comprising levofloxacin is administered in combination with active agents or compounds to achieve additive or synergistic effects in the alleviation or treatment of the syndromes or diseases.

In one embodiment, the pharmaceutical composition comprising levofloxacin is administered in combination with other agents such as a carrier, diluent, adjuvant, excipient, and vehicle, or other non-active agents.

In one embodiment, the pharmaceutical composition comprising levofloxacin is delivered to the subject via one of the routes including, but are not limited to, oral, nasal, sublingual, buccal, systemic, transdermal and mucosal.

In one embodiment, the pharmaceutical composition comprising levofloxacin is formulated into different dosage forms including, but are not limited to, tablets, granules, injection, powder, solution, suspension, sprays, patches or capsules.

In another embodiment, the pharmaceutical composition comprising levofloxacin is formulated into sustained-release compositions.

The present invention provides a method of alleviating or treating a metabolic syndrome or disease in a subject, the method comprises the step of administering to the subject an effective amount of a pharmaceutical composition comprising levofloxacin having the structure

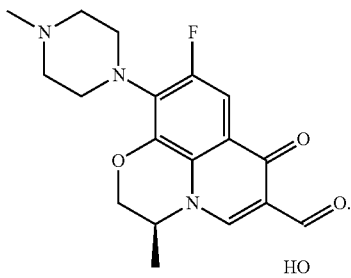

In one embodiment of the method of alleviating or treating a metabolic syndrome or disease, the method results in one or more of the following:
reduce the level of triglycerides in blood;
reduce the level of fasting plasma glucose;
reduce the blood pressure;
reduce the resistance to insulin;
reduce the degree of obesity;
reduce the degree of diabetes; and
increase the level of high-density lipoprotein.

In one embodiment of the method of alleviating or treating a metabolic syndrome or disease, the method inhibits human fatty acid binding protein 4. In another embodiment, the method inhibits adipolysis in adipocytes. In one embodiment, the method does not induce adipogenesis in adipocytes.

In one embodiment, the concentration of levofloxacin is about 10 µM.

In one embodiment, the pharmaceutical composition is administered in combination with other active or non-active agents. In another embodiment, the pharmaceutical composition is administered in combination with a carrier, diluent, adjuvant, excipient, or vehicle.

In one embodiment, the pharmaceutical composition is formulated in the form of tablets, granules, injection, powder, solution, suspension, sprays, patches, or capsules.

In one embodiment, the present invention provides a method of inhibiting fatty acid binding protein 4 in a subject, the method comprises the step of administering to the subject an effective amount of a pharmaceutical composition comprising levofloxacin having the structure

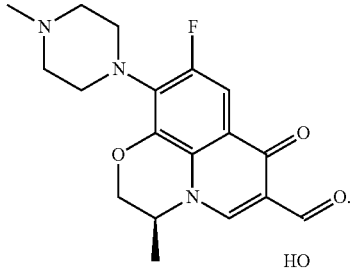

In one embodiment of the method of inhibiting fatty acid binding protein 4, the method results in one or more of the following:
reduce the level of triglycerides in blood;
reduce the level of fasting plasma glucose;
reduce the blood pressure;
reduce the resistance to insulin;
reduce the degree of obesity;
reduce the degree of diabetes; and
increase the level of high-density lipoprotein.

In one embodiment of the method of inhibiting fatty acid binding protein 4, the method does not induce adipogenesis in adipocytes.

In one embodiment, the concentration of levofloxacin is about 10 µM.

In one embodiment, the pharmaceutical composition is administered in combination with other active or non-active agents. In another embodiment, the pharmaceutical composition is administered in combination with a carrier, diluent, adjuvant, excipient, or vehicle.

In one embodiment, the pharmaceutical composition is formulated in the form of tablets, granules, injection, powder, solution, suspension, sprays, patches, or capsules.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

Molecular Docking Screening

This example illustrates one embodiment of molecular docking screening to identify novel FABP4 inhibitors from an FDA-approved drugs database containing about 1500 compounds. The workflow chart of the screening and analysis is illustrated in FIG. 1A.

Ligands Preparation for Docking Screening

For establishment of the ligands library, approximately 1500 FDA approved drugs were compiled based on DrugBank (accessed Nov. 30, 2012). The simplified molecular-input line-entry system (SMILES) format of phytochemicals was compiled from PubChem (accessed Nov. 30, 2012) or SciFinder (accessed Nov. 30, 2012). The SMILES format of compounds was converted to PDB (Protein Data Bank) format by CORINA online service (accessed Nov. 30, 2012). The PDB format of compounds was then converted to PDBQT ((Protein Data Bank, Partial Charge (Q) & Atom Type (T)) format by AutoDock Tools 1.5.6 (The Scripps Research Institute, CA, USA).

Target Proteins Preparation for Docking Screening

For the preparation of receptor, crystal structures of human FABP4 were obtained from the Protein Data Bank [PDB ID: 1TOU (19), 1TOW (7), 2NNQ (20) and 3FR5 (21)]. Both ligands and water molecules in target proteins were removed by Chimera 1.7 mac (UCSF Resource for Biocomputing, Visualization, and Informatics, CA, USA).

Then the hydrogen and Kollman Charges were added to the target protein by AutoDock Tools 1.5.6. The atoms of target protein were assigned as AD4 type, and the modified protein was converted to PDBQT format for docking screening.

Docking Parameters Validation

The docking parameters for AutoDock Vina were kept to their default values. The grid box was 20 Å×14 Å×12 Å, encompassing the inhibitor binding cavity of FABP4. The binding modes were clustered through the root-mean square deviation (RMSD) among the Cartesian coordinates of the ligand atoms. The docking results were ranked by the binding free energy. Inhibitors from the original protein models were extracted for parameter validation. It was observed in the docking simulation that the predicted conformations of inhibitors are close to the experimental conformations of inhibitors. Furthermore, the inhibitors exhibited high binding scores against human FABP4.

Results and Discussion

To reduce the rate of false positive, different FABP4-inhibitor complex structures were incorporated to partially compensate for target flexibility in the present computational study. Generally, four human FABP4 models were selected for molecular docking screening, including 1TOU (19), 1TOW (7), 2NNQ (20) and 3FR5 (21) from Protein Data Bank. The complete docking ranking lists obtained from the AutoDock Vina were summarized in Table S1 of the Supporting Information of Wang et al., 2014 (36). A total of top 30 ligands from each protein model were selected; and the average binding energies were calculated according to the scores of four different models. The top 10 candidates were filtered as potential FABP4 inhibitors from FDA-approved drugs and summarized in Table 1.

drugs (24). Darifenacin and fosaprepitant are newly approved drugs that are not commercially available.

The remaining five chemicals were then examined. As shown in Table 1, three antipsychotic drugs, paliperidone, risperidone and pimozide (25), all exhibited high binding affinities to human FABP4 in the analysis of molecular docking, whereas only pimozide directly inhibits FABP4 activity by in vitro validations. Two antibiotics, trovafloxacin and levofloxacin showed strong inhibitory effects on FABP4 activity. Trovafloxacin is a broad-spectrum antibiotic that blocks the activity of DNA gyrase and topoisomerase IV in various bacteria (26). Trovafloxacin inhibits 57.46±12.18% FABP4 activity at 10 µM, indicating that it might function as a FABP4 inhibitor. The most potent FABP4 inhibitor from our screening is levofloxacin with an inhibition on FABP4 activity of 70.01±12.15% at 10 µM.

Figure 1B:
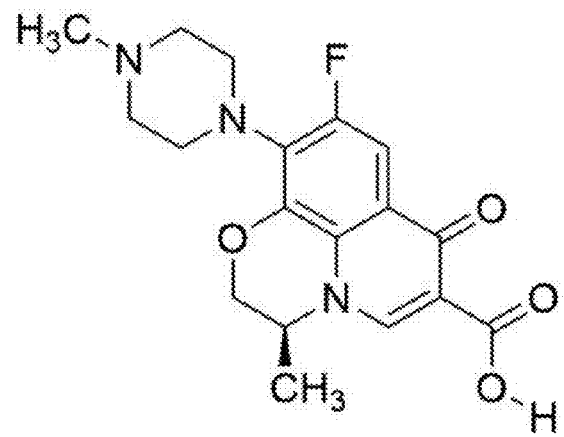

FIG. 1B showed the chemical structure of levofloxacin. Levofloxacin is a chiral fluorinated carboxyquinolone and is the 3,9-enantiomer of the racemic drug ofloxacin. Levofloxacin is a broad spectrum antibiotic for treating a series of infections including respiratory tract infections, cellulitis, and urinary tract infections (27, 28). Levofloxacin was found to significantly reduce pulmonary inflammation and there the medical indication of levofloxacin could expand to include asthma and cystic fibrosis (29).

Figures 1C, 1D:
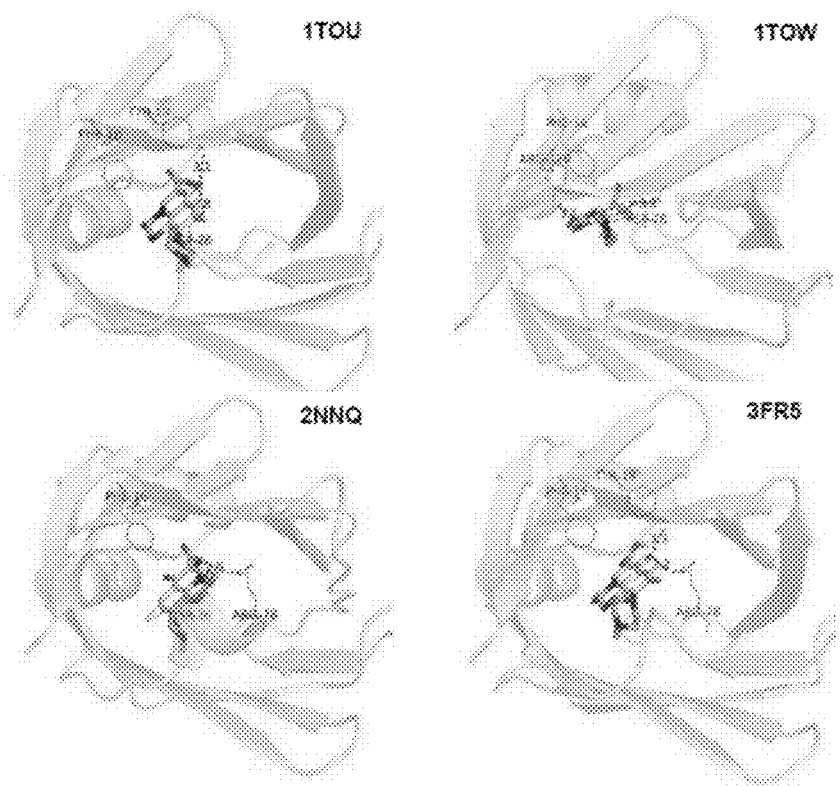

As illustrated in the docking result of FIGS. 1C and 1D, levofloxacin (stick) is found to bind to FABP4 (ribbon cartoon) with reasonable binding affinities in all of the four protein models (FIGS. 1C and 1 D). Bindings between the benchmark molecules and FABP4 in the four reference protein models were also examined in the present analysis.

TABLE 1

Top 10 candidates identified as potential FABP4 inhibitors by molecular docketing screening

| Rank | FDA approved drugs | Docking score (kcal/mol) | | | | | Commercially available | % FABP4 inhibition (10 µM) | Medical uses |
|---|---|---|---|---|---|---|---|---|---|
| | | 2NNQ | 1TOU | 1TOW | 3FR5 | Average | | | |
| 1 | Paliperidone | −10.9 | −11.1 | −10.8 | −10.3 | −10.8 | Yes | 5.12 ± 6.90 | Antipsychotic drug |
| 2 | Risperidone | −10.5 | −10.9 | −10.6 | −10.1 | −10.5 | Yes | 1.64 ± 12.90 | Antipsychotic drug |
| 3 | Fluorescein | −10.2 | −10.3 | −10.7 | −10.1 | −10.3 | No | ND | Fluorescent tracer |
| 4 | Pimozide | −10.9 | −10.0 | −9.4 | −10.5 | −10.2 | Yes | 46.98 ± 11.34 | Antipsychotic drug |
| 5 | Ketazolam | −9.9 | −10.4 | −10.8 | −9.6 | −10.2 | No | ND | Antipsychotic and antispasmodic drug |
| 6 | Levofloxacin | −10.7 | −9.8 | −10.0 | −9.9 | −10.1 | Yes | 70.01 ± 12.15 | Broad spectrum antibiotics |
| 7 | Trovafloxacin | −10.6 | −10.0 | −9.3 | −10.4 | −10.1 | Yes | 57.46 ± 12.18 | Broad spectrum antibiotics |
| 8 | Darifenacin | −9.8 | −10.0 | −10.5 | −9.8 | −10.0 | No | ND | Treat urinary incontinence |
| 9 | Antrafenine | −10.8 | −9.6 | −8.5 | −10.6 | −9.9 | No | ND | Analgesic and anti-inflammatory drug |
| 10 | Fosaprepitant | −10.2 | −9.9 | −9.6 | −9.8 | −9.9 | No | ND | Antiemetic drug |

Among the top 10 ranked hits, fluorescein is extensively used as a fluorescent tracer in diagnostic application. It is unlikely to be a drug for disease treatment for its serious adverse reactions, including cardiac arrest and anaphylactic shock (22). Ketazolam, a benzodiazepine derivative, is used for the treatment of anxiety. However, long-term administration of ketazolam results in tolerance and physical dependence. Currently, ketazolam is not approved for sale in Australia, United Kingdom or the United States (23). Antrafenine, a phenylpiperazine derivative, is marketed as an analgesic and anti-inflammatory drug, but is not widely used which is replaced by next generation anti-inflammatory Below are the analyses of the docket results.

In the 1TOU model, the benchmark molecule is 2-[4-hydroxy-6-(trifluoromethyl)pyrimidin-2-yl]sulfanyl-1-piperidin-1-yl-ethanone (B1V) (19). Based on the present docking simulation, B1V formed three critical hydrogen bonds with Tyr19, Arg126 and Tyr128 of FABP4. The π-π interaction cannot be observed in the B1V-FABP4 binding mode. Levofloxacin directly bound to Tyr19 and Asp79 through hydrogen bonds. In addition, levofloxacin also formed π-π interaction with Phe16. The calculated binding affinities of levofloxacin and B1V are −9.8 kcal/mol and −8.2 kcal/mol, respectively.

In the 1TOW model, the benchmark is 4-carbazol-9-ylbutanoic acid (CRZ) (7). The docking simulation showed that CRZ interacted with FABP4 through hydrogen bonds with Arg126 and Tyr128 of FABP4 as well as π-π interaction with Phe16 and Phe57. Levofloxacin formed hydrogen bonds with both Asp76 and Arg126. The π-π interaction between benzoxazine of ligand and a benzene ring of Phe16 contributed the high binding affinity of levofloxacin with FABP4.

In the 2NNQ model, the benchmark is 2-[3-[2-(5-ethyl-3,4-diphenyl-pyrazol-1-yl)phenyl]phenoxy]ethanoic acid (T4B) (20). The docking score of T4B is −11.1 kcal/mol, indicating that T4B might tightly bind to FABP4. The binding mode of T4B showed that Arg106, Arg126 and Tyr128 of FABP4 were key residues and formed hydrogen bonds with the ligand. Additionally, a strong π-π interaction between T4B and Phe57 were observed in the optimal binding mode. In the same protein model, levofloxacin bound to FABP4 with high binding score (−10.7 kcal/mol) through π-π interaction with Phe16 as well as hydrogen bonds with Asp76 and Arg78, respectively.

In the 3FR5 model, the benchmark is 5-(3-carbamoylbenzyl)-5,6,7,8,9,10-hexahydrocyclohepta[b]indole-4-carboxylic acid (I4A) (21). I4A interacted with Ser55, Arg126 and Tyr128 through hydrogen bonds and formed π-π interaction with Phe16. The docking simulation using the same protein model showed that levofloxacin formed hydrogen bonds with both Tyr19 and Arg78 of FABP4 as well as π-π interaction with Phe16.

Figure 2:
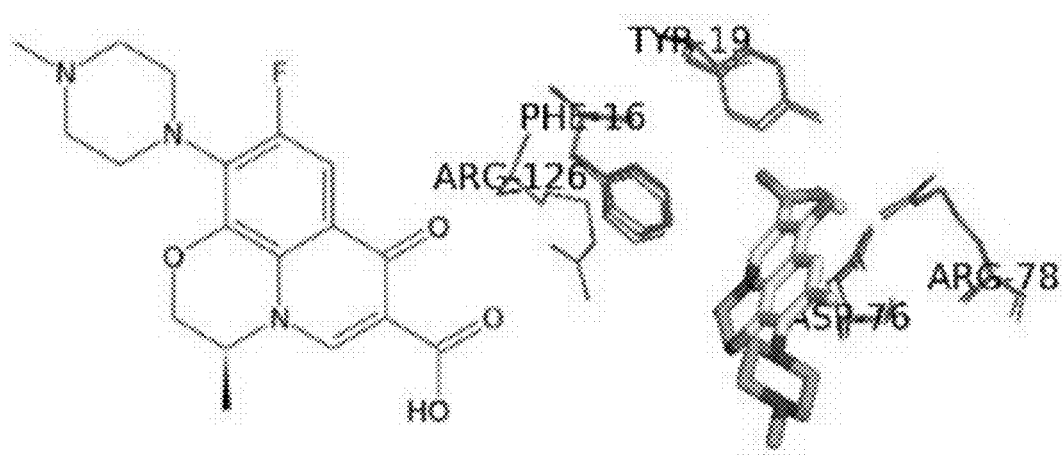
FIG. 2 shows the chemical structure of levofloxacin (left panel) and five amino acid residues of FABP4 (line) that may interact with levofloxacin (stick) (right panel).

Taken the above observations together, it is noticed that Arg126 and Tyr128 are common residues to form hydrogen bonds with known FABP4 ligands, whereas Phe16 and Phe57 are common residues to form π-π interactions with the ligands. However, levofloxacin is likely to form hydrogen bonds with Tyr19, Asp76 and Arg78. Furthermore, Phe16 has been identified as the most significant residue that can interact with levofloxacin through π-π interaction in all of four FABP4 protein models. FIG. 2 shows the five amino acid residues of FABP4 (Phe16, Tyr 19, Asp76, Arg78 and Arg126) that may interact with levofloxacin (stick) as indicated by the present docking results.

Example 2

Cell-Free Screening for FABP4-Inhibiting Activity

This example examined the FABP4-inhibiting activity of levofloxacin using a cell-free ligand displacement fluorescence-labeled probe assay.

The binding activities against human FABP4 were evaluated using FABP4 Inhibitor/Ligand Screening Assay Kit (Cayman Chemical: 10010231, MI, US). Briefly, the kit provided a detection reagent that exhibits increased fluorescence when bound to FABP4. Any FABP4 ligand will displace the detection reagent, thereby reduce the fluorescence. The test chemicals (levofloxacin, trovafloxacin, pimozide, risperidone and paliperidone) were purchased from Sigma (St. Louis, Mo.). Experiments were conducted according to the user manual, and the fluorescence signal at 370 nm (excitation)/475 nm (emission) was determined by SpectraMax® i3 Multi-Mode Microplate Reader (Molecular Devices, CA, USA).

Results and Discussion

Figure 3A:
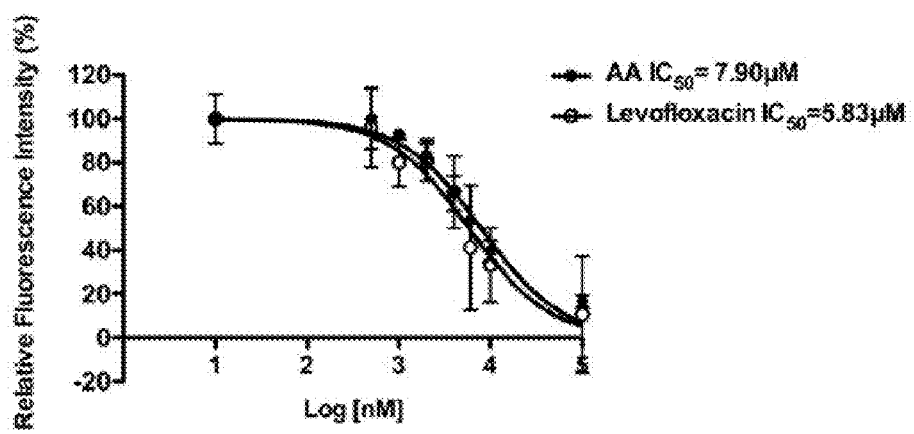
FIGS. 3A-3E describe the FABP4-inhibiting activity of levofloxacin examined using cell-free and cell-based assays.

FIG. 3A shows the dose-response curves of levofloxacin in FABP4 activity inhibition assay. Arachidonic acid (AA) which is an endogenous ligand of FABP4 (30) was used as a positive control. The $IC_{50}$ values were calculated using the inhibitor dose-response function in Prism 5.

It was found that levofloxacin directly inhibited FABP4 activity with an $IC_{50}$ value of 5.83 μM. The inhibitory activity of levofloxacin is similar to that of arachidonic acid ($IC_{50}$ of 7.90 μM).

Example 3

Cell-Based Functional Assays

This example examined the FABP4-inhibiting activities of levofloxacin using cell-based functional assays.

Cell Cultures

Mouse 3T3-L1 pre-adipocytes were cultured in Dulbecco's Modified Eagle's Medium (DMEM) supplemented with 10% fetal bovine serum, 100 units/ml penicillin and 100 μg/ml streptomycin at 37° C. in a humidified 95% air and 5% CO2 atmosphere. All cell culture reagents were purchased from Invitrogen (Carlsbad, Calif., USA). To initiate 3T3-L1 adipocyte differentiations, the standard differentiation cocktail (250 nM dexamethasone, 100 mM 3-isobutyl-1-methylxanthine and 175 nM human insulin, all purchased from Sigma, St. Louis, Mo.) was added to the medium after 2 days post-confluence. After 2 days, the medium was replaced with fresh complete medium containing insulin. Culture medium was changed every 2 days. Levofloxacin or benzbromarone (BBR) (Sigma, St. Louis, Mo.) was dissolved in DMSO and added to the medium at the beginning of pre-adipocyte differentiations. The DMSO level was less than 0.1% in culture medium, which did not affect the pre-adipocyte differentiation.

Adipolysis Assay

Confluent 3T3-L1 pre-adipocytes (day 0) were stimulated by the differentiation cocktail and cultured for 2 days with culture medium (Control), 10 μM of levofloxacin (Levofloxacin) or 10 μM benzbromarone (BBR). At day 2, the culture medium was collected and the extent of adipolysis was evaluated using Adipolysis Assay Kit (Cayman Chemical: 10009381, MI, US). During adipolysis, triglycerides are hydrolysed to release free fatty acids and glycerol. The amount of glycerol released into the medium as measured by the kit is proportional to the degree of adipolysis.

Figure 3B:
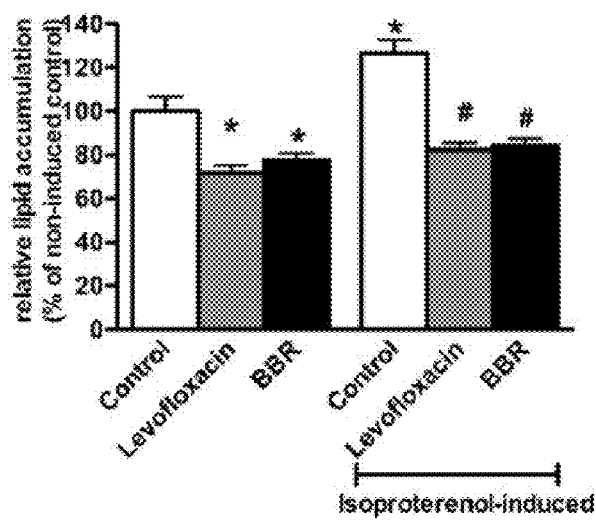

Basal adipolysis and isoproterenol-induced adipolysis were studied. Isoproterenol was included as a positive control for screening pharmaceuticals that are known to regulate the adipolysis. Cells were treated with 100 nM of isoproterenol for 24 hours after the treatment with culture medium, levofloxacin or benzbromarone. Results were repeated at least three times from three independent experiments and presented as mean±SD, n=3 (FIG. 3B). The results were statistically analyzed by one-way ANOVA test. *, P<0.05; compared with the control group. #, P<0.05; compared with the isoproterenol-treated group.

Cell Viability (MTT Assay)

Figure 3C:
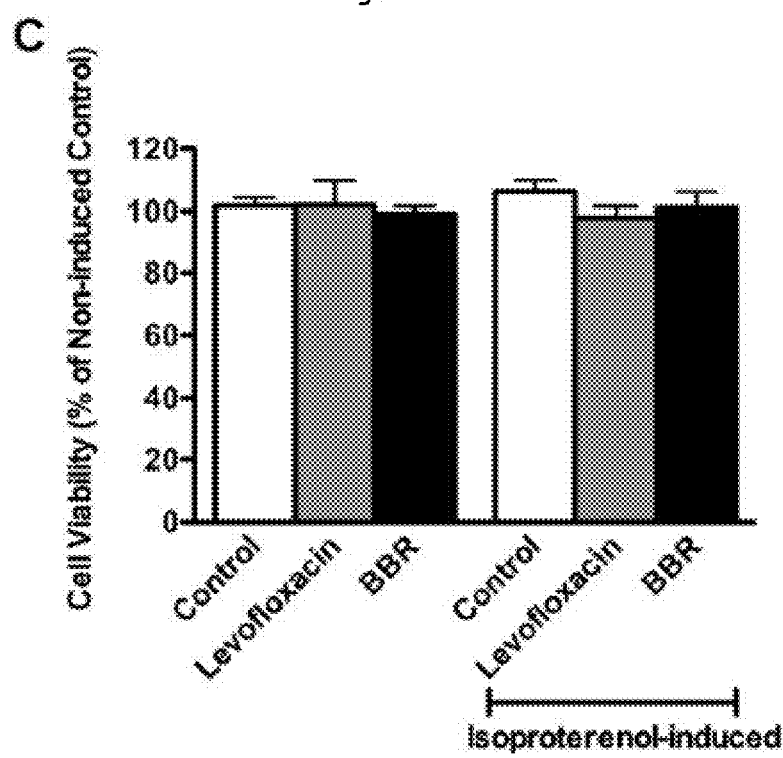

To evaluate the cytotoxicity of levofloxacin on 3T3-L1, a tetrazolium dye MTT colorimetric assay was performed to determine the cell viability. Briefly, 3T3-L1 cells were treated with levofloxacin for 24 h followed by incubation with isoproterenol (100 nM) for another 24 h. The viability was then measured by the MTT assay. Results were repeated at least three times from three independent experiments and presented as mean±SD, n=3. The results were statistically analyzed by one-way ANOVA test and plotted in FIG. 3C.

Oil Red O Staining

Figure 3D:
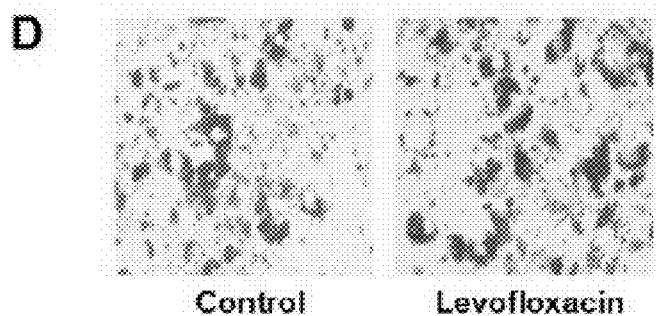

The 3T3-L1 cells were seeded in 12-well plates. Two days post-confluence (Day 0), the cells were stimulated to differentiate using the differentiation cocktail, and then treated with levofloxacin at 10 μM. All the samples were collected at Day 6. Briefly, the culture medium was removed and the cells were washed with PBS twice. The cells were fixed in 4% formalin in PBS for 30 minutes. The formalin was removed and the fixed cells were washed with PBS twice. The cells were stained with 0.5% Oil Red O(Sigma, St. Louis, Mo.) for 20 minutes. The lipid droplets in cells were characterized as red dots. After staining, the cells were washed with PBS and stained with hematoxylin for 10 seconds and then photographed macroscopically (FIG. 3D). Results were repeated at least three times from three independent experiments.

Western Blot Detection

Figure 3E:
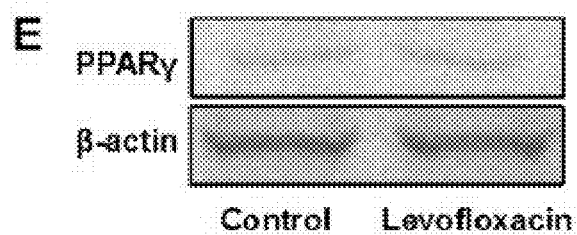

As in the above Oil Red O Staining assay, cells were harvested on Day 6 and the total protein was collected for western blotting to estimate the PPARγ protein level in the treated 3T3-L1 cells. Proteins in the total cell lysate of the treated cells were separated by 10% SDS polyacrylamide gel electrophoresis and electrotransferred to a polyvinylidene difluoride membrane (Immobilon-P membrane; Millipore, Bedford, Mass.). After blocking the blot with a solution of milk, membranes were incubated overnight with primary antibodies against PPARγ or β-actin (Santa Cruz Biotechnology, Santa Cruz, Calif., USA) followed by an incubation with alkaline phosphatase-conjugated antibodies for 1 hour. Specific bands were detected using 3-bromo-4-chloro-5-indolyl phosphate (BCIP) and nitro blue tetrazolium (NBT) system (Bio-Rad, Hercules, Calif.) and photographed (FIG. 3E). Results were repeated at least three times from three independent experiments.

Results and Discussion

Inhibition of Adipolysis (Adipolysis Assay)

It has been reported that the inhibition of FABP4 by pharmacological agents or genetic approaches decreased the adipolysis in 3T3-L1 cells. For example, benzbromarone (BBR) is a newly identified FABP4 inhibitor which inhibits the adipolysis at 10 μM (31). In the present example, the effect on adipolysis of levofloxacin was examined. The results showed that levofloxacin given at 10 μM inhibited both the basal adipolysis and isoproterenol-stimulated adipolysis in 3T3-L1 cells (FIG. 3B). The inhibitory effects were also observed in the BBR-treated groups, suggesting that levofloxacin may modulate the hydrolysis of triglycerides or the level of lipids by inhibiting FABP4.

Rising blood glucose and insulin levels have been identified as critical indicators of obesity-induced insulin resistance and type 2 diabetes. It was observed in a study that obese wild-type mice exhibited higher blood glucose levels compared to lean controls. However, on the high-fat diet, FABP4-deficiency mice had significantly lower blood glucose concentrations compared to wild-type controls (32). Interestingly, severe hypoglycemia has been reported associated with levofloxacin treatment in type 2 diabetic patients receiving polytherapy (33-35). The observed hypoglycaemia in type 2 diabetic patients may be attributed by the FABP4 inhibitory effects of levofloxacin, as firstly demonstrated in the present study.

Cell Viability (MTT Assay)

The results of MTT assay (FIG. 3C) indicated that proliferation of 3T3-L1 cells were not affected by 10 μM of levofloxacin or BBR regardless of the isoproterenol treatment, suggesting that both compounds did not impose any cytotoxic effects on the cells.

Induction of Adipogenesis (Oil Red O Staining)

Recent study demonstrated that BMS309403, a well-known FABP4 inhibitor, when binding to FABP4 might lead to an allosteric regulation of FABP4, therefore resulting in the elevation of PPARγ protein expression as well as the induction of adipogenesis in adipocytes (9).

Adipogenesis is a cell differentiation process from pre-adipocytes into adipocytes which may directly promote the development of obesity. Here, levofloxacin was tested for its capability of acting as an allosteric inhibitor to promote adipogenesis in 3T3-L1 cells.

Levofloxacin was added at the beginning of induction of differentiation of 3T3-L1 cells and kept in the medium throughout the differentiation period (days 0-6). At the end of treatment, cells were fixed with formalin and stained with 0.5% Oil Red O. The lipid droplets in cells were characterized as red dots. As shown in FIG. 3D, there was no significant difference of red dots between the levofloxacin-induced group and the control group, indicating that levofloxacin did not promote lipid accumulation in adipocytes.

Effect of PPARγ Protein Expression (Western Blot)

Effects of levofloxacin treatment on protein expression levels of PPARγ were also studied. The protein levels of PPARγ in the cell lysates of untreated and levofloxacin-treated groups were compared. FIG. 3E shows that addition of levofloxacin did not increase the protein expression of PPARγ. These results indicate that levofloxacin treatment during adipocyte differentiation has no impact on adipogenesis in 3T3-L1 cells, suggesting that levofloxacin is not an allosteric inhibitor of FABP4 as BMS309403.

Taken all the results of Examples 1-3 together, levofloxacin may directly bind to the fatty acid binding pocket of FABP4 and inhibit FSBP4, and does not induce an allosteric regulation of FABP4 and up-regulation of PPARγ.

In summary, the present invention for the first time identified levofloxacin as an inhibitor of FABP4. After an initial molecular docking screening, biochemical characterizations were conducted to assess the role of levofloxacin in modulating or inhibiting FABP4. The results suggested that levofloxacin directly inhibited FABP4 and may be used to reduce the extent of adipolysis or the level of blood glucose. Furthermore, levofloxacin did not induce adipogenesis in adipocytes, therefore prevents or alleviates the development of obesity which is the major adverse effect of FABP4 inhibitors.

As a results of the FABP4 inhibiting activities of levofloxacin demonstrated above and proven safety for human consumption, the present invention provides the uses of levofloxacin as a FABP4 inhibitor to modulate cellular or physiological activities that are mediated by the FABP4 or responsive to the FABP4 inhibition. In one embodiment, the present invention provides the uses of levofloxacin as a drug to alleviate or treat metabolic diseases or cardiovascular diseases including, but are not limited to, insulin resistance, diabetes, obesity and atherosclerosis.

REFERENCES

1. Boden, G., Obesity, Insulin Resistance and Free Fatty Acids. *Curr Opin Endocrinol Diabetes Obes* 2011, 18, 139-143.
2. Karpe, F.; Dickmann, J. R.; Frayn, K. N., Fatty Acids, Obesity, and Insulin Resistance: Time for a Reevaluation. *Diabetes* 2011, 60, 2441-2449.
3. Smit, E. N.; Muskiet, F. A.; Boersma, E. R., The Possible Role of Essential Fatty Acids in the Pathophysiology of Malnutrition: A Review. *Prostaglandins Leukot Essent Fatty Acids* 2004, 71, 241-250.

4. Boord, J. B.; Fazio, S.; Linton, M. F., Cytoplasmic Fatty Acid-Binding Proteins: Emerging Roles in Metabolism and Atherosclerosis. *Curr Opin Lipidol* 2002, 13, 141-147.
5. Furuhashi, M.; Hotamisligil, G. S., Fatty Acid-Binding Proteins: Role in Metabolic Diseases and Potential as Drug Targets. *Nat Rev Drug Discov* 2008, 7, 489-503.
6. Furuhashi, M.; Tuncman, G.; Gorgun, C. Z.; Makowski, L.; Atsumi, G.; Vaillancourt, E.; Kono, K.; Babaev, V. R.; Fazio, S.; Linton, M. F.; Sulsky, R.; Robl, J. A.; Parker, R. A.; Hotamisligil, G. S., Treatment of Diabetes and Atherosclerosis by Inhibiting Fatty-Acid-Binding Protein Ap2. *Nature* 2007, 447, 959-965.
7. Lehmann, F.; Haile, S.; Axen, E.; Medina, C.; Uppenberg, J.; Svensson, S.; Lundback, T.; Rondahl, L.; Barf, T., Discovery of Inhibitors of Human Adipocyte Fatty Acid-Binding Protein, a Potential Type 2 Diabetes Target. *Bioorg Med Chem Lett* 2004, 14, 4445-4448.
8. Adida, A.; Spener, F., Adipocyte Type Fatty Acid-Binding Protein as Inter-Compartmental Shuttle for Peroxisome Proliferator Activated Receptor Gamma Agonists in Cultured Cell. *Biochim Biophys Acta* 2006, 1761, 172-181.
9. Garin-Shkolnik, T.; Rudich, A.; Hotamisligil, G. S.; Rubinstein, M., Fabp4 Attenuates Ppargamma and Adipogenesis and Is Inversely Correlated with Ppargamma in Adipose Tissues. *Diabetes* 2014, 63, 900-911.
10. Ahmadian, M.; Suh, J. M.; Hah, N.; Liddle, C.; Atkins, A. R.; Downes, M.; Evans, R. M., Ppargamma Signaling and Metabolism: The Good, the Bad and the Future. *Nat Med* 2013, 19, 557-566.
11. Leung, C. H.; Chan, D. S.; Kwan, M. H.; Cheng, Z.; Wong, C. Y.; Zhu, G. Y.; Fong, W. F.; Ma, D. L., Structure-Based Repurposing of FDA-Approved Drugs as Tnf-Alpha Inhibitors. *Chem Med Chem* 2011, 6, 765-768.
12. Ma, D. L.; Chan, D. S.; Leung, C. H., Drug Repositioning by Structure-Based Virtual Screening. *Chem Soc Rev* 2013, 42, 2130-2141.
13. Zhong, H. J.; Liu, L. J.; Chan, D. S.; Wang, H. M.; Chan, P. W.; Ma, D. L.; Leung, C. H., Structure-Based Repurposing of FDA-Approved Drugs as Inhibitors of Nedd8-Activating Enzyme. *Biochimie* 2014, 102, 211-215.
14. Bisson, W. H., Drug Repurposing in Chemical Genomics: Can We Learn from the Past to Improve the Future? *Curr Top Med Chem* 2012, 12, 1883-1888.
15. Ng, C.; Hauptman, R.; Zhang, Y.; Bourne, P. E.; Xie, L., Anti-Infectious Drug Repurposing Using an Integrated Chemical Genomics and Structural Systems Biology Approach. *Pac Symp Biocomput* 2014, 136-147.
16. Oprea, T. I.; Mestres, J., Drug Repurposing: Far Beyond New Targets for Old Drugs. *AAPS J* 2012, 14, 759-763.
17. Eberhard, Y.; McDermott, S. P.; Wang, X.; Gronda, M.; Venugopal, A.; Wood, T. E.; Hurren, R.; Datti, A.; Batey, R. A.; Wrana, J.; Antholine, W. E.; Dick, J. E.; Schimmer, A. D., Chelation of Intracellular Iron with the Antifungal Agent Ciclopirox Olamine Induces Cell Death in Leukemia and Myeloma Cells. *Blood* 2009, 114, 3064-3073.
18. Minden, M. D.; Hogge, D. E.; Weir, S. J.; Kasper, J.; Webster, D. A.; Patton, L.; Jitkova, Y.; Hurren, R.; Gronda, M.; Goard, C. A.; Rajewski, L. G.; Haslam, J. L.; Heppert, K. E.; Schorno, K.; Chang, H.; Brandwein, J. M.; Gupta, V.; Schuh, A. C.; Trudel, S.; Yee, K. W.; Reed, G. A.; Schimmer, A. D., Oral Ciclopirox Olamine Displays Biological Activity in a Phase I Study in Patients with Advanced Hematologic Malignancies. *Am J Hematol* 2014, 89, 363-368.
19. Ringom, R.; Axen, E.; Uppenberg, J.; Lundback, T.; Rondahl, L.; Barf, T., Substituted Benzylamino-6-(Trifluoromethyl)Pyrimidin-4(1h)-Ones: A Novel Class of Selective Human a-Fabp Inhibitors. *Bioorg Med Chem Lett* 2004, 14, 4449-4452.
20. Sulsky, R.; Magnin, D. R.; Huang, Y.; Simpkins, L.; Taunk, P.; Patel, M.; Zhu, Y.; Stouch, T. R.; Bassolino-Klimas, D.; Parker, R.; Harrity, T.; Stoffel, R.; Taylor, D. S.; Lavoie, T. B.; Kish, K.; Jacobson, B. L.; Sheriff, S.; Adam, L. P.; Ewing, W. R.; Robl, J. A., Potent and Selective Biphenyl Azole Inhibitors of Adipocyte Fatty Acid Binding Protein (Afabp). *Bioorg Med Chem Lett* 2007, 17, 3511-3515.
21. Barf, T.; Lehmann, F.; Hammer, K.; Haile, S.; Axen, E.; Medina, C.; Uppenberg, J.; Svensson, S.; Rondahl, L.; Lundback, T., N-Benzyl-Indolo Carboxylic Acids: Design and Synthesis of Potent and Selective Adipocyte Fatty-Acid Binding Protein (a-Fabp) Inhibitors. *Bioorg Med Chem Lett* 2009, 19, 1745-1748.
22. Ha, S. O.; Kim, D. Y.; Sohn, C. H.; Lim, K. S., Anaphylaxis Caused by Intravenous Fluorescein: Clinical Characteristics and Review of Literature. *Intern Emerg Med* 2014, 9, 325-330.
23. Charleston, L. t., Burning Mouth Syndrome: A Review of Recent Literature. *Curr Pain Headache Rep* 2013, 17, 336.
24. Leatham, P. A.; Bird, H. A.; Wright, V.; Seymour, D.; Gordon, A., A Double Blind Study of Antrafenine, Naproxen and Placebo in Osteoarthrosis. *Eur J Rheumatol Inflamm* 1983, 6, 209-211.
25. Bak, M.; Fransen, A.; Janssen, J.; van Os, J.; Drukker, M., Almost All Antipsychotics Result in Weight Gain: A Meta-Analysis. *PLoS One* 2014, 9, e94112.
26. Goldstein, E. J., Possible Role for the New Fluoroquinolones (Levofloxacin, Grepafloxacin, Trovafloxacin, Clinafloxacin, Sparfloxacin, and Du-6859a) in the Treatment of Anaerobic Infections: Review of Current Information on Efficacy and Safety. *Clin Infect Dis* 1996, 23 Suppl 1, S25-30.
27. Davis, R.; Bryson, H. M., Levofloxacin. A Review of Its Antibacterial Activity, Pharmacokinetics and Therapeutic Efficacy. *Drugs* 1994, 47, 677-700.
28. Wimer, S. M.; Schoonover, L.; Garrison, M. W., Levofloxacin: A Therapeutic Review. *Clin Ther* 1998, 20, 1049-1070.
29. Michael N. Dudley, R. Y. T., David C. Griffith, Olga Rodny Topical Use of Levofloxacin for Reducing Lung Inflammation. 2010.
30. Gillilan, R. E.; Ayers, S. D.; Noy, N., Structural Basis for Activation of Fatty Acid-Binding Protein 4. *J Mol Biol* 2007, 372, 1246-1260.
31. Cai, H. Y.; Wang, T.; Zhao, J. C.; Sun, P.; Yan, G. R.; Ding, H. P.; Li, Y. X.; Wang, H. Y.; au, W. L.; Chen, K. X., Benzbromarone, an Old Uricosuric Drug, Inhibits Human Fatty Acid Binding Protein 4 in Vitro and Lowers the Blood Glucose Level in Db/Db Mice. *Acta Pharmacol Sin* 2013, 34, 1397-1402.
32. Maeda, K.; Cao, H.; Kono, K.; Gorgun, C. Z.; Furuhashi, M.; Uysal, K. T.; Cao, Q.; Atsumi, G.; Malone, H.; Krishnan, B.; Minokoshi, Y.; Kahn, B. B.; Parker, R. A.; Hotamisligil, G. S., Adipocyte/Macrophage Fatty Acid Binding Proteins Control Integrated Metabolic Responses in Obesity and Diabetes. *Cell Metab* 2005, 1, 107-119.
33. Friedrich, L. V.; Dougherty, R., Fatal Hypoglycemia Associated with Levofloxacin. *Pharmacotherapy* 2004, 24, 1807-1812.
34. Kanbay, M.; Aydogan, T.; Bozalan, R.; Isik, A.; Uz, B.; Kaya, A.; Akcay, A., A Rare but Serious Side Effect of Levofloxacin: Hypoglycemia in a Geriatric Patient. *Diabetes Care* 2006, 29, 1716-1717.
35. Singh, N.; Jacob, J. J., Levofloxacin and Hypoglycemia. *Clin Infect Dis* 2008, 46, 1127.
36. Wang, Y.; Law, W. K.; Hu, J. S.; Lin, H. Q.; Ip, T. M.; Wan, D. C., Discovery of FDA-approved drugs as inhibitors of fatty acid binding protein 4 using molecular docking screening. *J Chem Inf Model*. 2014, 54:3046-50.

What is claimed is:

1. A method of alleviating or treating a cardiovascular disease in a subject, comprising the step of administering to the subject an effective amount of a pharmaceutical composition comprising levofloxacin having the structure:

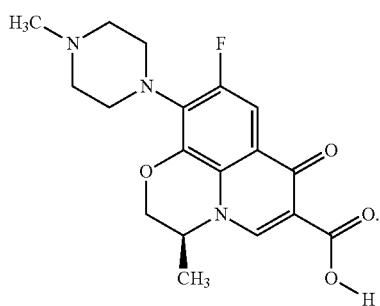 [SMILES: C[C@H]1COc2c(N3CCN(C)CC3)c(F)cc3c(=O)c(C(=O)O)cn1c23]

2. The method of claim 1, wherein the method results in one or more of the following:
   reduce the level of triglycerides in blood;
   reduce the level of fasting plasma glucose;
   reduce the blood pressure;
   reduce the resistance to insulin;
   reduce the degree of obesity;
   reduce the degree of diabetes; and
   increase the level of high-density lipoprotein.

3. The method of claim 1, wherein the cardiovascular disease is selected from the group consisting of atherosclerosis, coronary artery diseases, angina, myocardial infarction, stroke, hypertensive heart disease, cardiomyopathy, peripheral artery disease and venous thrombosis.

4. The method of claim 1, wherein the cardiovascular disease is a heart or blood vessel disease that is related to a metabolic process mediated by the fatty acid binding protein 4.

5. The method of claim 1, wherein the method inhibits human fatty acid binding protein 4.

6. The method of claim 1, wherein the method inhibits adipolysis in adipocytes.

7. The method of claim 1, wherein the method does not induce adipogenesis in adipocytes.

8. The method of claim 1, wherein the concentration of levofloxacin is about 10 μM.

9. The method of claim 1, wherein the pharmaceutical composition is administered in combination with other active or non-active agents.

10. The method of claim 1, wherein the pharmaceutical composition is administered in combination with a carrier, diluent, adjuvant, excipient, or vehicle.

11. The method of claim 1, wherein the pharmaceutical composition is formulated in the form of tablets, granules, injection, powder, solution, suspension, sprays, patches, or capsules.

12. A method of inhibiting fatty acid binding protein 4 in a cell, comprising the step of contacting the cell with an effective amount of a pharmaceutical composition comprising levofloxacin having the structure

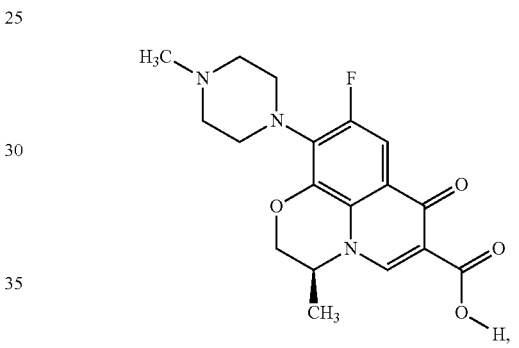

wherein the concentration of levofloxacin is about 10 μM.

13. The method of claim 12, wherein the method inhibits adipolysis in adipocytes.

14. The method of claim 12, wherein the cell is 3T3-L1.

* * * * *